United States Patent [19]

Spector

[11] 4,346,059
[45] Aug. 24, 1982

[54] AROMA-GENERATING LAMP STRUCTURE

[76] Inventor: Donald Spector, 380 Mountain Rd., Union City, N.J. 07087

[21] Appl. No.: 240,165

[22] Filed: Mar. 3, 1981

[51] Int. Cl.³ .............................................. A61L 9/04
[52] U.S. Cl. .................................... 422/125; 239/34; 239/56; 239/57; 422/4; 422/187; 422/306
[58] Field of Search ................... 422/124, 125, 4, 305, 422/306, 187; 239/34, 56, 57

[56] References Cited

U.S. PATENT DOCUMENTS

| | | | |
|---|---|---|---|
| 658,793 | 10/1900 | Lockey | 422/125 X |
| 1,403,548 | 1/1922 | Gudeman | 422/125 |
| 1,706,939 | 3/1929 | Rosenthal | 422/125 |
| 2,515,310 | 7/1950 | Messina | 422/125 |
| 2,591,818 | 4/1952 | Huff | 422/125 |
| 2,618,892 | 11/1952 | Locks et al. | 239/53 X |
| 2,942,090 | 6/1960 | Diehl | 422/125 X |
| 3,080,624 | 3/1963 | Weber | 422/125 |
| 3,119,650 | 1/1964 | Bilyeu | 422/125 |
| 3,330,481 | 7/1967 | Dearling | 239/57 X |
| 3,864,080 | 2/1975 | Valbona et al. | 422/4 |
| 3,972,473 | 8/1976 | Harrison | 239/34 |
| 4,084,732 | 4/1978 | Dearling | 239/34 X |

FOREIGN PATENT DOCUMENTS

| | | | |
|---|---|---|---|
| 2807383 | 8/1978 | Fed. Rep. of Germany | 239/60 |
| 1443314 | 7/1976 | United Kingdom | 239/34 |

Primary Examiner—Barry S. Richman
Attorney, Agent, or Firm—Michael Ebert

[57] ABSTRACT

An aroma-generating lamp structure including an electric bulb mounted on a base and enclosed by a shell which is at least partially translucent, whereby the shell functions as a light shade, the shell being spring-mounted on the base and therefore being depressible. Socketed on the base is a bottle filled with a liquid scent, the bottle being coupled to a pump having an actuating head which cooperates with the shell so that when the shell is depressed, liquid is sprayed onto an absorbent pad disposed within the shell in the proximity of the bulb. Heat from the bulb vaporizes the liquid to generate an aroma which is exuded through vents in the shell.

11 Claims, 5 Drawing Figures

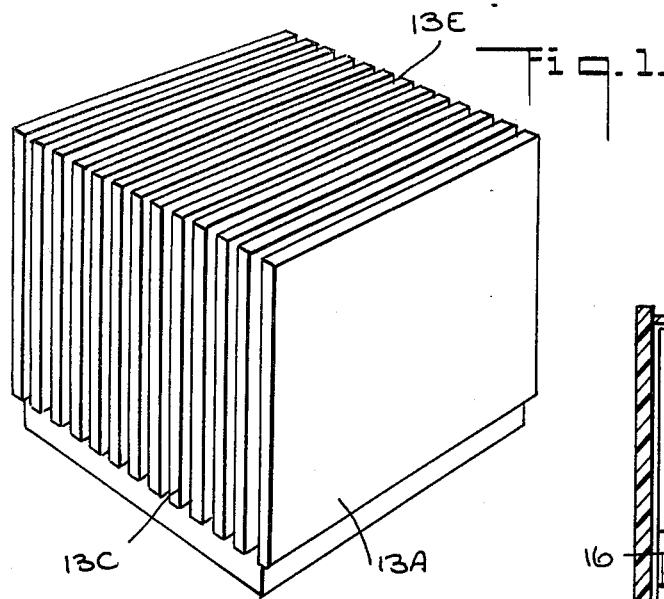
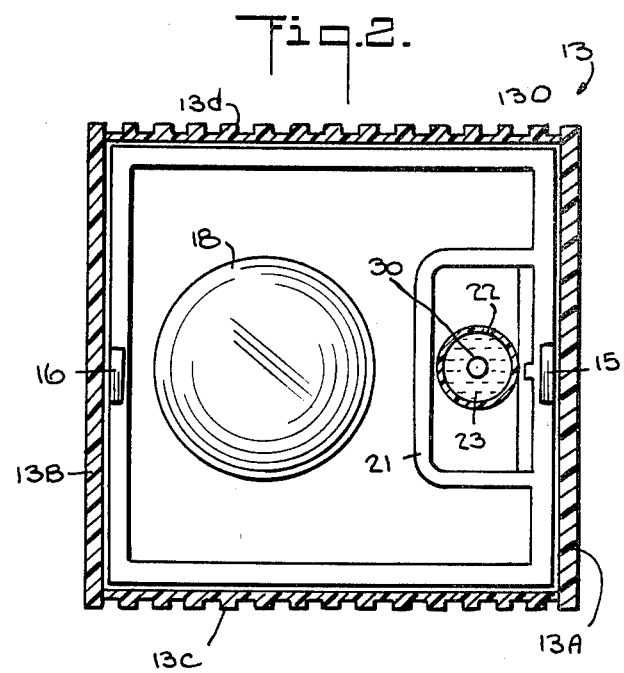
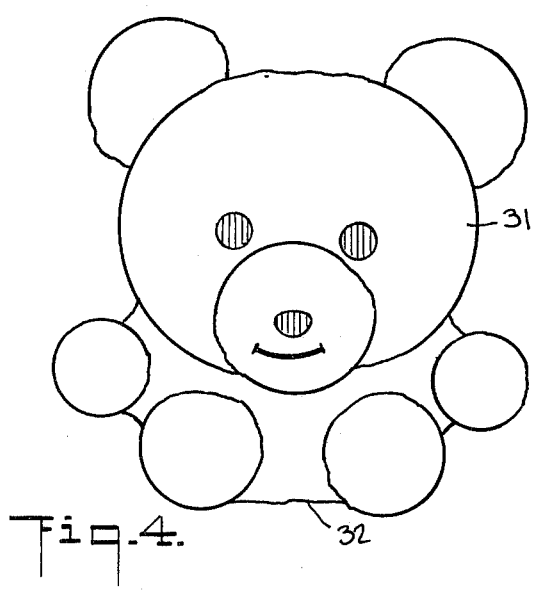
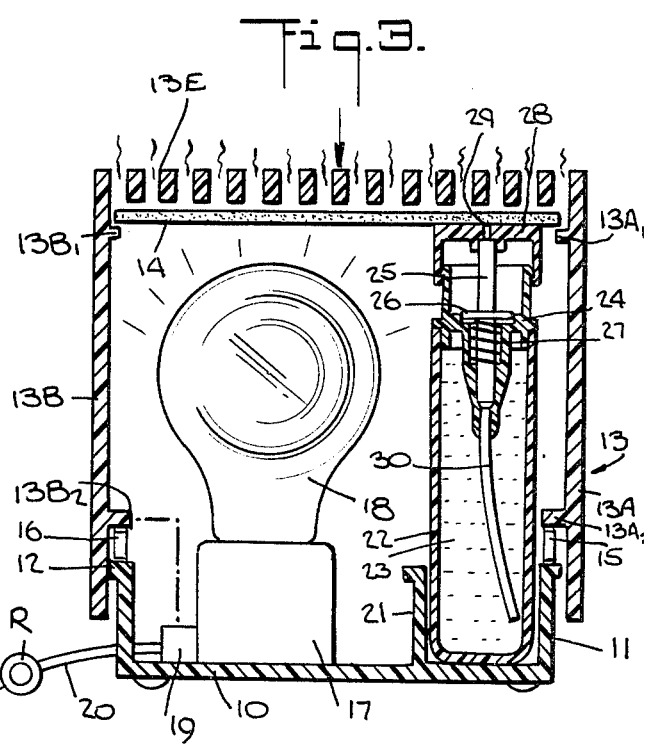
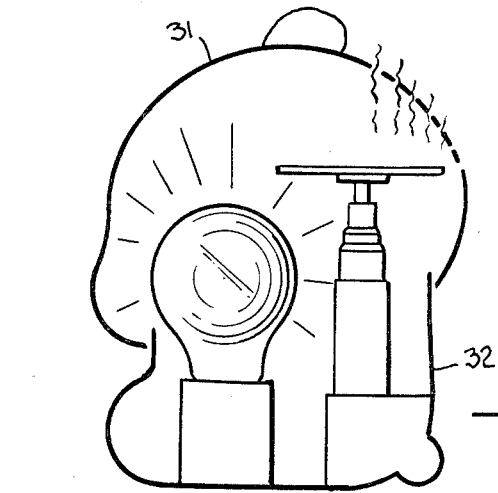

AROMA-GENERATING LAMP STRUCTURE

BACKGROUND OF INVENTION

This invention relates generally to aroma-generators, and more particularly to an electric lamp structure in which a bulb is housed within a translucent shell which also encloses an actuatable liquid aroma dispenser, the bulb serving to vaporize the dispensed liquid to produce the desired aroma which is exuded through the shell.

As used herein, the term "aroma" is not limited to pleasant or savory smells, but encompasses scents that function as insecticides, air fresheners, deodorants or any other odor that acts to condition, modify or otherwise charge the atmosphere.

The aroma of perfumes and perfume-based products such as colognes and toilet waters was originally derived from the essential oils of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents the ingredients are combined with alcohol.

Various types of spray devices or dispensers are known for emitting aromas. Thus the patent to Dearling U.S. Pat. No. 4,084,732, disclosed a dispenser for wafting into the atmosphere in insecticide, a pleasant smelling scent or any other aroma, this being accomplished by means of a pressurized container. When the actuating button of this container is pressed, a dispersant is released onto an absorbent material, the absorbent dispersant permeating the atmosphere.

Similarly, the Sekiguchi et al U.S. Pat. No. 3,679,133 discloses a perfume dispenser which includes a sponge-like head that receives and exudes a charge of perfume. In the spray aerosol can disclosed in the Harrison U.S. Pat. No. 3,972,473, an absorptive ring is impregnated with an air-freshening fragrance and released into the atmosphere. U.S. Pat. Nos. 1,921,821; 3,410,488; and 3,441,353 are along similar lines, for they show wicks and other absorptive materials to accept and emit a perfume or other odoriferous liquid.

In my prior U.S. Pat. No. 4,200,229, entitled, "Aroma-Dispensing Cartridge and Holder Assembly," the assembly is designed for installation in an automobile interior for charging this interior with a pleasant or stimulating fragrance. The cartridge includes a bottled filled with a liquid scent, a suction pump being supported on the stopper of the bottle. When actuated, the pump sprays the scent into a pad of absorbent material.

The difficulty with an aroma dispenser which functions to spray a charge of liquid onto a pad of absorbent material is that at ambient temperature the liquid, even when it has a high alcohol content, is slow to volatilize; hence the resultant odor, though of sufficient strength in the confines of an automotive interior, may lack adequate intensity in those environments which are relatively open, such as the living room or bedroom of a home.

It is known to promote vaporization of aroma-producing liquids by means of an electric bulb which also generate heat. Thus the Eisner U.S. Pat. No. 2,372,371 shows a pad saturated with a deodorant held in a small container mounted directly on the bulb. Similar bulb arrangements to promote vaporization are disclosed in the Gudeman U.S. Pat. No. 1,403,548; the Fusay et al. U.S. Pat. No. 2,557,501; and the Schlesinger U.S. Pat. No. 2,435,756.

In bulb-operated aroma dispensers of the type heretofore known, the bulb acts primarily to afford a source of heat to promote vaporization in an arrangement in which the light emitted from the naked bulb represents an incidental effect that does not provide light in an acceptable form for a household. Moreover, there is no cooperation between the operation of the bulb and the aroma-producing liquid, for when the bulb is switched on, an aroma will then be produced only if there is liquid in the pad or whatever other source is provided. This liquid supply may be exhausted at the time the bulb is put into operation.

SUMMARY OF INVENTION

In view of the foregoing, the main object of this invention is to provide in a lamp structure, a bulb enclosed in a vented housing which is at least partially translucent and serves, therefore, as a lamp shade, the housing also enclosing an actuatable liquid fragrance dispenser which is actuated simply by applying manual pressure to the housing, the bulb also functioning through its heat to vaporize the dispensed liquid to produce an aroma which is exuded through the vents.

More particularly, an object of this invention is to provide a structure of the above type which functions both to illuminate a room and to freshen or scent the air thereof, which structure permits easy replacement of the bulb and replenishment of the liquid fragrance supply.

Also an object of this invention is to provide a lamp structure which includes an aroma dispenser in an arrangement wherein each time the lamp is turned on, a charge of aroma-producing liquid is sprayed onto a pad of absorbent material.

Yet another object of the invention is to provide a structure of the above type which may be manufactured at low cost and which operates efficiently and reliably.

Briefly stated, these objects are attained in an aroma-generating lamp structure including an electric bulb mounted on a base and enclosed by a shell which is at least partially translucent, whereby the shell functions as a light shade, the shell being spring-mounted on the base and therefore being depressible. Socketed on the base is a bottle filled with a liquid scent, the bottle being coupled to a pump having an actuating head which cooperates with the shell so that when the shell is depressed, liquid is sprayed onto an absorbent pad disposed within the shell in the proximity of the bulb. Heat from the bulb vaporizes the liquid to generate an aroma which is exuded through vents in the shell.

OUTLINE OF DRAWINGS

For a better understanding of the invention as well as other objects and further features thereof, reference is made to the following detailed description to be read in conjunction with the accompanying drawings, wherein:

FIG. 1 is a perspective view in somewhat schematic form of a box-like lamp structure which includes an aroma dispenser in accordance with the invention;

FIG. 2 is a transverse section taken through FIG. 1;

FIG. 3 is a longitudinal section taken through FIG. 1;

FIG. 4 is a perspective view of a lamp structure in accordance with the invention having a teddy bear configuration; and FIG. 5 is a longitudinal section taken through the FIG. 4 structure.

DESCRIPTION OF INVENTION

Referring now to FIGS. 1 to 3, there is shown a first embodiment of a lamp structure in accordance with the invention, the structure comprising a square base 10 having side walls 11 whose upper edge is provided with a lip 12, and a shell 13 which telescopes over the base, so that the resultant structure is cubical in form.

Shell 13 is composed of a pair of planar end panels 13A and 13B which may be opaque, a pair of ribbed side panels 13C and 13D which are formed of translucent material, and a similarly-ribbed top panel 13E, the spacings between the ribs of the top panel having pores or vents therein to exude a fragrance. In practice, both the shell and base of the cube may be molded of synthetic plastic, translucent material such as polypropylene or polycarbonate having acceptable structural properties, the end panels being rendered opaque by the application thereto of a light-impermeable coating which may also take the form of a decorative pattern that is abstract or figurative.

Formed on the inner surfaces of side panels 13A and 13B are two pairs of ledges; the first pair $13A_1$ and $13B_1$ being adjacent the top panel 13E in a plane parallel thereto; and the second pair $13A_2$ and $13B_2$ being adjacent and parallel to the lip 12 of the base.

Ledges 13A and 13B serve to support the edges of a pad of absorbent material 14 having wicking properties such as a foam plastic or polyurethane material. Interposed between ledges $13A_2$ and $13B_2$ and lip 12 are leaf springs 15 and 16 which provide a resilient mounting for shell 13 whereby the shell is depressible.

Anchored on base 10 is a conventional screw-type socket 17 for a light bulb 18 which is energized through a microswitch 19, also mounted on base 10. Power is supplied to bulb 18 by a cable 20 connected to the socket in series with the switch so that the light bulb is turned on or off only when switch 19 is actuated. Switch 19 is operatively linked to ledge $13B_2$, whereby when manual pressure is first applied to top panel 13E, the switch is turned on; and when again applied, the switch is turned off.

Also formed on base 10 is a rectangular socket 21 adapted to nest a bottle 22 having a similar rectangular shape, the bottle being filled with an aroma-producing liquid 23. Bottle 22 is closed by a removable stopper 24. Supported on stopper 24 is a suction pump that includes a hollow piston 25 that is axially shiftable. Piston 25 is normally maintained at its extended position at which its free end is projected beyond a cylindrical upper collar 26 extension of the stopper by a biasing spring 27, the collar being concentric with the piston.

Telescopically received over collar 26 is a cylindrical actuator head 28 having a central inlet 29 adapted to retain the free end of piston 25. The other end of the plunger communicates with a flexible pipe 30 extending into the bottle to draw fluid therefrom. The suction pump mechanism is of the type commonly used in spray bottles such as those containing a liquid window cleaner sold commercially under the Windex mark.

Alternatively, the liquid container may be of the standard aerosol type having an aerosol valve actuated by an appropriate plunger mechanism having a head comparable to head 28. In any case, head 28 is positioned just below pad 14 so that when pressure is applied to top panel 13E by an operator, not only is bulb 18 turned on, but head 28 is depressed to operate the pump to produce a spray of liquid which is directed toward the underside of the pad, the liquid being wicked thereby to saturate the pad.

Because of heat generated by lamp 18 which lies below the pad, impregnating the pad is volatilized to produce vapors which are exuded through the vents in top panel 13E. Thus each time the lamp is turned on or off, the charge of liquid in the pad is replenished automatically. While the supply in the pad may be close to exhaustion when the lamp is kept on for a prolonged period, when the lamp is turned off, a fresh charge is sprayed onto the pad, the charge being wicked throughout the pad, so that the next time the lamp is turned, vaporization of the liquid proceeds to take place shortly thereafter.

When the supply of liquid in the bottle is exhausted, it can readily be replenished by lifting shell 13 above the base to expose the bottle, which can then be removed from its socket 21 for refilling.

Thus the structure shown in FIGS. 1 and 2 function not only as a shaded lamp suitable, for example, as a night light, but also as a room freshener. For this purpose, the housing of the lamp may also include a compact ion generator of the type currently available on the market to produce an abundant supply of negative ions.

In the arrangement shown in FIGS. 4 and 5, the housing for the structure takes the form of a simulated rigid teddy bear constituted by a depressible shell 31 which is spring-mounted on a base 32, the shell being shaped in the form of the bear's head and the base in the form of the bear's torso, legs and hands. The shell is molded of translucent plastic material provided with vents, and the base is molded of opaque plastic material.

Incorporated within the teddy-bear structure is a bulb, a liquid dispenser and pad in essentially the same arrangement as in the first embodiment, so that when the shell is depressed, the bulb is turned on or off and the dispenser is actuated. The invention is obviously not limited to a teddy bear or box-like configuration and it may assume any desired form constituted by a depressible shell telescopically received over a base.

It is important that the operating distinctions between a pad saturated with an aroma-producing liquid clipped onto a bulb, as in the prior art, and a boxed arrangement in accordance with the invention be clearly understood.

In the prior arrangement, the heat generated is radiated in all directions and no pressure is applied to cause the heated air to flow primarily through the pad to promote volatilization. In the present invention, the bulb or other heat-producing element is confined within a housing and the heat generated therein causes the air to expand to create a pressure differential between the heated air in the housing and the atmosphere. As a consequence, hot air under pressure which can escape, mainly through the vents in the shell, is necessarily first forced through the saturated pad below the vents, thereby promoting rapid volatilization of the liquid fragrance.

This pressurized action serves to prevent clogging of the pores of the pad by the liquid fragrance, the tendency toward clogging being greatest with relatively heavy oil-based perfumes. The pressure also acts to effect a full discharge of the liquid from the pad so that the same pad may later be used without fear of contamination for a different liquid fragrance.

In order to adjust the amount of heat generated, a rheostat R may be interposed in the power line to reduce or decrease the heat output, as desired, and thereby vary the rate at which fragrance is emitted. While a heat source in the form of a bulb which also produces light is disclosed, in practice a heater element which creates no visible light may also be used where the object is only to generate a fragrance.

I claim:

1. An aroma-generating structure comprising:
   A a substantially enclosed housing having a vent at the top thereof;
   B a pad of porous material having wicking properties completely covering said vent, said pad being impregnated with an aroma-producing liquid; and
   C an electrical heating means confined within the housing, said means acting to heat and expand the confined air to create a positive air pressure in the housing producing a pressure differential between the heated air and the atmosphere above said vent, thereby driving the heated air through the pad-covered vent to rapidly volatilize the liquid and exude an aromatic vapor into the atmosphere.

2. A structure as set forth in claim 1, wherein said housing is at least partially translucent and said heating means is an electric lamp.

3. An aroma-generating structure comprising:
   A a base having a spring-biased shell telescopically mounted thereon to create a substantially enclosed housing, said shell being depressible;
   B a bottle containing an aroma-producing liquid mounted on the base;
   C dispenser means associated with the bottle and including an actuator head operatively coupled to the shell whereby when the shell is depressed, liquid is sprayed toward the shell;
   D a pad of absorbent material supported within the shell at a position thereon adjacent an inner wall of the shell to receive the liquid spray, said pad having wicking properties to cause said liquid to spread throughout the pad, said inner wall having vents therein which are completely covered by the pad to exude vapors released from the pad; and
   E an electric heater supported on the base at a position wherein the heat produced thereby creates a positive air pressure in the housing which produces a differential pressure between the heated air in the housing and the atmosphere outside the vents, thereby driving the heated air through said pad into said vents to rapidly vaporize the liquid, said vents representing the only escape path from the housing whereby the aromatic vapor is exuded into the atmosphere.

4. A structure as set forth in claim 3, wherein said dispenser means is a suction pump.

5. A structure as set forth in claim 3, wherein said dispenser means is an aerosol valve.

6. A structure as set forth in claim 3, wherein said shell has a box-like form and said pad is supported thereon adjacent the top wall of the shell.

7. A structure as set forth in claim 3, further including means to vary the amount of heat produced by said heater.

8. A structure as set forth in claim 3, wherein said heater is an electric lamp and said shell is at least partially formed of translucent material.

9. A structure as set forth in claim 8, further including a switch to operate said lamp mounted on said base and operatively coupled to the shell, whereby when said shell is depressed, said lamp is turned on or off.

10. A structure as set forth in claim 3, further including a socket on said base to nest said bottle.

11. A structure as set forth in claim 10, wherein said bottle and the socket therefor have a rectangular cross section.

* * * * *